(12) United States Patent
Deane et al.

(10) Patent No.: US 7,686,870 B1
(45) Date of Patent: Mar. 30, 2010

(54) EXPANDABLE PRODUCT RATE PORTABLE GAS FRACTIONALIZATION SYSTEM

(75) Inventors: Geoffrey Frank Deane, Goleta, CA (US); Lawrence Howes, Santa Barbara, CA (US); Brenton Alan Taylor, Kenwood, CA (US)

(73) Assignee: Inogen, Inc., Goleta, CA (US)

( * ) Notice: Subject to any disclaimer, the term of this patent is extended or adjusted under 35 U.S.C. 154(b) by 664 days.

(21) Appl. No.: 11/618,393

(22) Filed: Dec. 29, 2006

Related U.S. Application Data

(60) Provisional application No. 60/755,591, filed on Dec. 29, 2005.

(51) Int. Cl.
*B01D 53/02* (2006.01)

(52) U.S. Cl. ............... 96/115; 96/130; 128/205.12; 128/205.27

(58) Field of Classification Search ............... 95/1, 95/23, 96; 128/205.12, 205.27
See application file for complete search history.

(56) References Cited

U.S. PATENT DOCUMENTS

| | | | |
|---|---|---|---|
| 2,195,565 A | 4/1940 | Fricke | |
| 2,728,407 A | 12/1955 | Squier | |
| 2,798,718 A | 7/1957 | Gross | |
| 2,944,627 A | 7/1960 | Skarstrom | |
| 3,258,899 A | 7/1966 | Coffin | |
| 3,323,292 A | 6/1967 | Brown | |
| 3,406,501 A | 10/1968 | Watkins | |
| 3,703,068 A | 11/1972 | Wagner | |
| 3,730,158 A | 5/1973 | St. Amand | |
| 3,880,616 A | 4/1975 | Myers et al. | |
| 3,922,149 A | 11/1975 | Ruder et al. | |
| 3,976,050 A | 8/1976 | Glasser et al. | |
| 4,054,133 A | 10/1977 | Meyers | |
| 4,070,164 A | 1/1978 | Miwa et al. | |
| 4,077,779 A | 3/1978 | Sircar et al. | |
| 4,146,277 A | 3/1979 | Santoro | |
| 4,222,750 A | 9/1980 | Gauthier et al. | |
| 4,247,311 A | 1/1981 | Seibert et al. | |
| 4,302,224 A | 11/1981 | McCombs et al. | |
| 4,303,419 A | 12/1981 | Frank et al. | |
| 4,342,573 A | 8/1982 | McCombs et al. | |
| 4,371,384 A | 2/1983 | McCombs | |

(Continued)

FOREIGN PATENT DOCUMENTS

EP         0 848 981         6/1998

(Continued)

*Primary Examiner*—Robert A Hopkins
(74) *Attorney, Agent, or Firm*—Knobbe, Martens, Olson & Bear, LLP

(57) ABSTRACT

An oxygen concentrator system that includes or can be expanded to include more than one compressor is provided. The system utilizes a controller that is adapted to selectively activate or deactivate one or more of the compressors to optimize system performance and efficiency. Multiple compressors can be selected to operate at the same time, thereby enabling the system to operate at a higher peak pressure, increase the recovery of the PSA cycle, and expand the product rate. The additional compressors can also be removed when not in use so as to reduce weight of the system. In some implementations, the system housing reserves a certain amount of space for accommodating additional compressors and related components, which can be added to the system as after market parts. In other implementations, the additional compressor can be located external to the system.

11 Claims, 4 Drawing Sheets

U.S. PATENT DOCUMENTS

| | | | |
|---|---|---|---|
| 4,373,938 A | 2/1983 | McCombs |
| 4,378,982 A | 4/1983 | McCombs |
| 4,381,002 A | 4/1983 | Mon |
| 4,428,372 A | 1/1984 | Beysel et al. |
| 4,449,990 A | 5/1984 | Tedford, Jr. |
| 4,462,398 A | 7/1984 | Durkan et al. |
| 4,482,361 A | 11/1984 | Whysall |
| 4,491,459 A | 1/1985 | Pinkerton |
| 4,496,376 A | 1/1985 | Hradek |
| 4,502,873 A | 3/1985 | Mottram et al. |
| 4,509,959 A | 4/1985 | McCombs |
| 4,511,377 A | 4/1985 | McCombs |
| 4,516,424 A | 5/1985 | Rowland |
| 4,534,346 A | 8/1985 | Schlaechter |
| 4,584,996 A | 4/1986 | Blum |
| 4,681,099 A | 7/1987 | Sato et al. |
| 4,686,974 A | 8/1987 | Sato et al. |
| 4,698,075 A | 10/1987 | Dechene |
| 4,706,664 A | 11/1987 | Snook et al. |
| 4,744,803 A | 5/1988 | Knaebel |
| 4,770,678 A | 9/1988 | Haslett, Jr. |
| 4,783,205 A | 11/1988 | Searle |
| 4,802,899 A | 2/1989 | Vrana et al. |
| 4,826,510 A | 5/1989 | McCombs |
| 4,877,429 A | 10/1989 | Hunter |
| 4,892,566 A | 1/1990 | Bansal et al. |
| 4,925,464 A | 5/1990 | Rabenau et al. |
| 4,971,609 A | 11/1990 | Pawlos |
| 5,002,591 A | 3/1991 | Stanford |
| 5,004,485 A | 4/1991 | Hamlin et al. |
| 5,005,570 A | 4/1991 | Perkins |
| 5,032,150 A | 7/1991 | Knaebel |
| 5,071,453 A | 12/1991 | Hradek et al. |
| 5,112,367 A | 5/1992 | Hill |
| 5,114,441 A | 5/1992 | Kanner et al. |
| 5,144,945 A | 9/1992 | Nishino et al. |
| 5,154,737 A | 10/1992 | Jenkins et al. |
| 5,226,933 A | 7/1993 | Knaebel et al. |
| 5,268,021 A | 12/1993 | Hill et al. |
| 5,275,642 A | 1/1994 | Bassine |
| 5,366,541 A | 11/1994 | Hill et al. |
| 5,427,609 A | 6/1995 | Zoglman et al. |
| 5,466,134 A | 11/1995 | Shaffer et al. |
| 5,474,595 A | 12/1995 | McCombs |
| 5,495,848 A | 3/1996 | Aylsworth et al. |
| 5,496,388 A | 3/1996 | Tellier |
| 5,531,807 A | 7/1996 | McCombs |
| 5,549,736 A | 8/1996 | Coffield et al. |
| 5,558,086 A | 9/1996 | Smith et al. |
| 5,578,115 A | 11/1996 | Cole |
| 5,593,478 A | 1/1997 | Hill et al. |
| 5,603,315 A | 2/1997 | Sasso, Jr. |
| 5,611,845 A | 3/1997 | Delp, II |
| 5,626,131 A | 5/1997 | Chua et al. |
| 5,630,411 A | 5/1997 | Holscher |
| 5,632,612 A | 5/1997 | Shaffer |
| 5,658,371 A | 8/1997 | Smolarek et al. |
| 5,665,316 A | 9/1997 | Salonia et al. |
| 5,697,364 A | 12/1997 | Chua et al. |
| 5,730,778 A | 3/1998 | Hill et al. |
| 5,735,268 A | 4/1998 | Chua et al. |
| 5,746,806 A | 5/1998 | Aylsworth et al. |
| 5,752,816 A | 5/1998 | Shaffer |
| 5,755,224 A | 5/1998 | Good et al. |
| 5,759,020 A | 6/1998 | Shaffer |
| 5,827,358 A | 10/1998 | Kulish et al. |
| 5,839,434 A | 11/1998 | Enterline |
| 5,865,174 A | 2/1999 | Kloeppel |
| 5,871,564 A | 2/1999 | McCombs |
| 5,881,725 A | 3/1999 | Hoffman et al. |
| 5,890,490 A | 4/1999 | Aylsworth et al. |
| 5,906,672 A | 5/1999 | Michaels et al. |
| 5,912,426 A | 6/1999 | Smolarek et al. |
| 5,917,135 A | 6/1999 | Michaels et al. |
| 5,928,189 A | 7/1999 | Phillips et al. |
| 5,968,236 A | 10/1999 | Bassine |
| 5,979,440 A | 11/1999 | Honkonen et al. |
| 5,997,617 A | 12/1999 | Czabala et al. |
| 6,033,457 A | 3/2000 | Lawless |
| 6,036,754 A | 3/2000 | Rowe |
| 6,050,792 A | 4/2000 | Shaffer |
| 6,068,680 A | 5/2000 | Kulish et al. |
| 6,077,331 A | 6/2000 | Phillips |
| 6,129,530 A | 10/2000 | Shaffer |
| 6,146,447 A | 11/2000 | Sircar et al. |
| 6,152,134 A | 11/2000 | Webber et al. |
| 6,176,897 B1 | 1/2001 | Keefer |
| 6,186,142 B1 | 2/2001 | Schmidt et al. |
| 6,190,441 B1 | 2/2001 | Czabala et al. |
| 6,192,884 B1 | 2/2001 | Vann et al. |
| 6,220,244 B1 | 4/2001 | McLaughlin |
| 6,269,811 B1 | 8/2001 | Duff et al. |
| 6,299,670 B1 | 10/2001 | Applegarth |
| 6,311,719 B1 | 11/2001 | Hill et al. |
| 6,342,090 B1 | 1/2002 | Cao |
| 6,346,139 B1 | 2/2002 | Czabala |
| 6,348,082 B1 | 2/2002 | Murdoch et al. |
| 6,371,114 B1 | 4/2002 | Schmidt et al. |
| 6,372,026 B1 | 4/2002 | Takemasa et al. |
| 6,395,065 B1 | 5/2002 | Murdoch et al. |
| 6,427,690 B1 | 8/2002 | McCombs et al. |
| 6,439,864 B1 | 8/2002 | Shaffer |
| 6,457,485 B2 | 10/2002 | Hill et al. |
| 6,478,850 B1 | 11/2002 | Warren |
| 6,497,755 B2 | 12/2002 | Murdoch et al. |
| 6,511,308 B2 | 1/2003 | Shaffer |
| 6,520,176 B1 | 2/2003 | Dubois et al. |
| 6,532,957 B2 | 3/2003 | Berthon-Jones |
| 6,532,958 B1 | 3/2003 | Buan et al. |
| 6,551,384 B1 | 4/2003 | Ackley et al. |
| 6,558,451 B2 | 5/2003 | McCombs et al. |
| 6,581,297 B1 | 6/2003 | Ginder |
| 6,629,525 B2 | 10/2003 | Hill et al. |
| 6,712,877 B2 | 3/2004 | Cao et al. |
| 6,712,886 B2 | 3/2004 | Kim |
| 6,764,534 B2 | 7/2004 | McCombs et al. |
| 6,805,122 B2 | 10/2004 | Richey et al. |
| 6,805,729 B2 | 10/2004 | Lim et al. |
| 6,811,590 B2 | 11/2004 | Lee et al. |
| 6,866,041 B2 | 3/2005 | Hardy et al. |
| 6,949,133 B2 * | 9/2005 | McCombs et al. ............ 96/111 |
| 7,066,985 B2 | 6/2006 | Deane et al. |
| 7,396,387 B2 * | 7/2008 | Baksh et al. .................. 95/96 |
| 2002/0053286 A1 | 5/2002 | Czabala |
| 2002/0121191 A1 | 9/2002 | Warren |
| 2003/0005928 A1 | 1/2003 | Appel et al. |
| 2003/0024531 A1 | 2/2003 | Ball |
| 2003/0167924 A1 | 9/2003 | McCombs et al. |
| 2003/0192431 A1 | 10/2003 | Lee et al. |
| 2004/0020366 A1 | 2/2004 | Walker et al. |
| 2004/0074496 A1 | 4/2004 | Hayashi et al. |
| 2004/0149133 A1 | 8/2004 | McCombs et al. |
| 2005/0072423 A1 | 4/2005 | Deane et al. |
| 2005/0072426 A1 | 4/2005 | Deane et al. |

FOREIGN PATENT DOCUMENTS

| | | |
|---|---|---|
| EP | 0 988 882 | 3/2000 |
| WO | WO 01 41900 | 6/2001 |

* cited by examiner

EXPANDABLE PRODUCT RATE PORTABLE GAS FRACTIONALIZATION SYSTEM

CROSS-REFERENCE TO RELATED APPLICATIONS

This application claims the benefit of priority under 35 U.S.C. §119(e) of U.S. Provisional Application No. 60/755,591 filed on Dec. 29, 2005, which is incorporated herein by reference in its entirety.

BACKGROUND OF THE INVENTION

1. Field of the Invention

This invention relates generally to gas concentrators, and in particular, to a concentrator system designed to allow simple expansion of the rate at which product gas is delivered. The application is particularly directed to portable oxygen concentrators for therapeutic use.

2. Description of the Related Art

The application of oxygen concentrators for therapeutic use is known, and many variants of such devices exist. A particularly useful class of oxygen concentrators is designed to be portable, allowing users to move about and to travel for extended periods of time without the need to carry a supply of stored oxygen. Most of these portable concentrators are based on pressure swing adsorption (PSA) designs which feed compressed air to selective adsorption beds. In a typical oxygen concentrator, the beds selectively adsorb nitrogen, resulting in pressurized, oxygen-rich product gas.

The main elements in an exemplary oxygen concentrator are shown in FIG. 1, which shows that air is drawn in and typically filtered at air inlet before being pressurized by compressor. The pressurized air is directed by a complex valve arrangement through adsorbent beds. An exemplary adsorbent bed implementation is comprised of three columns filled with zeolite powder. The pressurized air is directed through these columns in a series of steps which constitute a PSA cycle. Although many different arrangements of beds are possible as well as a variety of different PSA cycles, the typical result is that nitrogen is removed by the adsorbent material, and the resulting oxygen rich air is routed to a product gas storage. Some of the oxygen rich air is routed back through the bed to flush out the trapped nitrogen to an exhaust. Generally multiple beds, or columns in an exemplary device, are used so at least one bed may be used to make product while at least one other is being flushed, ensuring a continuous flow of product gas.

Such PSA systems are known in the art. It will also be appreciated that the gas flow control through the compressor and the beds in a PSA cycle is complex and requires precise timing and control of parameters such as pressure, temperature and oxygen concentration. Accordingly, most modern concentrators also have a programmable controller, typically a microprocessor, to monitor various parameters. Also present in most portable concentrators is a conserver which acts to ensure that oxygen rich gas is only delivered to a patient when a breath is inhaled, thus using less product than a continuous flow arrangement, which in turn allows for smaller and lighter concentrator designs. A typical concentrator will also include a user/data interface as shown in FIG. 1.

A portable oxygen concentrator should be small, light and quiet in order to be useful, while retaining the capacity to produce a flow of product gas, usually at a flow rate prescribed by a medical practitioner, adequate to provide for a patient's needs. Although fixed site stationary PSA based concentrators have been available for many years, such fixed site units may weigh fifty pounds or more, be several cubic feet in size and produce sound levels greater than 50 dbA. A portable concentrator on the other hand may weigh on the order of 10 lbs, be less than one half cubic foot in size and produce as little as 35-45 dbA sound levels. Yet portable concentrators still need to produce the prescribed flow rate. Thus, portable concentrator designs typically involve a significant amount of miniaturization, leading to smaller, more complex designs compared to stationary units. System size, weight, and complexity constraints for portable concentrators may also limit design choices for mitigating overheating and contamination.

In the design of such a concentrator, system optimization can be critical. Several metrics become important. Primary among these being system specific power, or the electric power input required per unit of product gas output. Weight of the device is another important metric. Characteristics which contribute to these metrics include: run time on a battery of a given size/weight, production of noise; vibration and heat which are strongly correlated to system power consumption; durability and impact requirement; and cost. Secondary considerations extend to efficiencies of PSA cycle operation, compressor function, motor function, and supporting electronic circuitry.

In optimizing the above parameters, oxygen concentrator designers are challenged to make trade-offs. For example, additional weight may allow the device to operate more efficiently. Alternatively, weight reduction may result in higher power consumption. Typically, system optimization requires the designer to provide a value function to each parameter, and then to work to maximize that value function through design trade-offs.

One difficulty that follows this design optimization process is the loss of flexibility. Once a specific design point is selected, the system often constrained. Constituent components, such as valves, tubing, compressor, motor, cooling fans or blowers, and circuit electronics may be selected to meet the needs of this optimized design, but when implemented, can restrict the system to operation over a narrow range. For example, an oxygen concentrator system may be designed to produce between 150 to 750 ml/min of 90% pure oxygen. Elements of the system may be capable of producing a higher top end rate when the entire system is designed with this in mind. For example, compressor/motor assemblies are often selected such that they operate near their limit when produced the specified maximum product flow. If the compressor/motor were over-sized, capable of providing more input gas flow to the PSA cycle, the adsorbent may be able to produce more product gas. However, the design would sacrifice in terms of weight, and would drop in efficiency at the lower flow rates, in exchange for this flexibility. Likewise, valves selected to allow up to a maximum flow rate may yield too much flow restriction when flow exceeds this value. Oversizing the valves may result in weight and power consumption penalties.

Pressure swing adsorption systems, well known in the art, utilize a cyclic pressurization and depressurization of chambers containing selective adsorbent. The efficiency of this system is typically measured in several metrics. The PSA recovery, R, is the product oxygen flow rate, $Q_p$, divided by the intake oxygen flow rate, or $$R = \frac{Q_P}{Q \times f_{o_2}}$$

where Q is the input air flow rate, and $f_{O2}$ is the fraction of oxygen in the intake air, typically about 21%. The Specific Power, $P/Q_p$, described above, is then a function of the air intake flow, Q, the pressure swing ratio $P_H/P_L$, the compressor efficiency, $h_c$, the motor/driver efficiency, $h_m$, and the ancillary power $P_A$, as shown in the following equation:

$$\frac{P}{Q_P} = \frac{\rho_{air} \times C_p \times T_{inlet} \times \left(\left(\frac{P_H}{P_L}\right)^{\frac{(\gamma-1)}{\gamma}} - 1\right)}{R \times f_{o_2} \times \eta_c \times \eta_m} + \frac{P_A}{Q_P}$$

In optimization, it may be possible to assign design value to the power and mass of specific solutions, producing an optimization curve relative to one or more design parameters. In general, design of a concentrator system is then completed at or near the optimal design point. Often, design is optimized across a range of operation, such as across the product rate of 0.15-0.75 slpm product delivery.

However, if design is carefully performed such that other systemic restrictions are minimized, other operating ranges may be achievable by the device with either minor modifications or by the addition of ancillary equipment. For example, tubing may be selected to be sufficiently large as to not produce restriction, circuit electronics may be designed to handle higher current loads, and valves may be configured to allow higher inlet and exhaust flows.

One of the objectives of the present invention is to provide design approaches which allow flexibility in operational parameters without requiring complete redesign of the concentrator device.

SUMMARY OF THE INVENTION

The preferred embodiments of the oxygen concentrator system have several features, no single one of which is solely responsible for their desirable attributes. Without limiting the scope of this invention, its more prominent features will now be discussed briefly. However, not all of the following features are necessary to achieve the advantages of the system. Therefore, none of the following features should be viewed as limiting. After considering this discussion, and particularly after reading the section entitled "Detailed Description of the Preferred Embodiments," one will understand how the features of the preferred embodiments provide advantages over prior art devices.

In one embodiment, the present invention provides an oxygen concentrator system comprising a plurality of compressors, a PSA unit in fluid communication with the compressors and a controller, wherein the controller is adapted to selectively activate or deactivate one or more of the plurality of compressors to optimize system performance and efficiency. In one implementation, each compressor is capable of producing compressed feed gas for the PSA unit, wherein the compressed feed gas stream from a first compressor is teed into the compressed feed gas stream from a second compressor. Preferably, the two compressor feed gas streams are connected by a check valve. In another implementation, the controller selectively activates more than one compressor to cause multiple compressors to operate at the same time, thereby enabling the system to operate at a higher peak pressure and increases the recovery of the PSA cycle. In yet another implementation, the controller selectively alternates activation and deactivation of a plurality of compressors to reduce the wear on a single compressor. Preferably, at least one of the compressors can be removed from the system when not in use so as to reduce overall weight of the system. In a preferred embodiment, the controller is capable of determining the number of compressors present in the system and adjusting the system algorithms and user interface according to the number of compressors present. The compressor can comprise internal and external compressors. In one implementation, the controller deactivates the internal compressor and utilizes the external compressor for feed gas. In another implementation, the controller selectively activates more than one compressor simultaneously to increase pressurized gas feed rate, thereby resulting in a higher gas delivery rate. Preferably, the plurality of compressors utilize the same drive electronics on the controller.

In another embodiment, the present invention provides an oxygen concentrator system comprising an enclosure defining a space, wherein a plurality of components are disposed in the space. The components together are sufficient to effectively operate the system. Preferably, a portion of the space is adapted to receive additional components that can be added to increase the capacity of the system. The system further includes a controller, wherein the controller is adapted to adjust system operating parameters and user interface when the additional components are added. In one implementation, the additional component comprises a compressor, preferably a piston compressor with a rotating motor. In another implementation, the additional components are preferably after market components.

In yet another embodiment, the present invention provides an expandable oxygen concentrator system comprising a compressor adapted to produce a pressurized feed gas, a PSA unit adapted to receive the pressurized feed gas from the compressor, and an optional compressor, wherein the optional compressor can be activated to increase system capacity. In one implementation, the optional compressor is positioned external to the system. In another implementation, the compressor and the PSA unit are contained in a system housing, wherein the system housing has a space reserved for the optional compressor.

DETAILED DESCRIPTION OF THE PREFERRED EMBODIMENT

Figure 1:
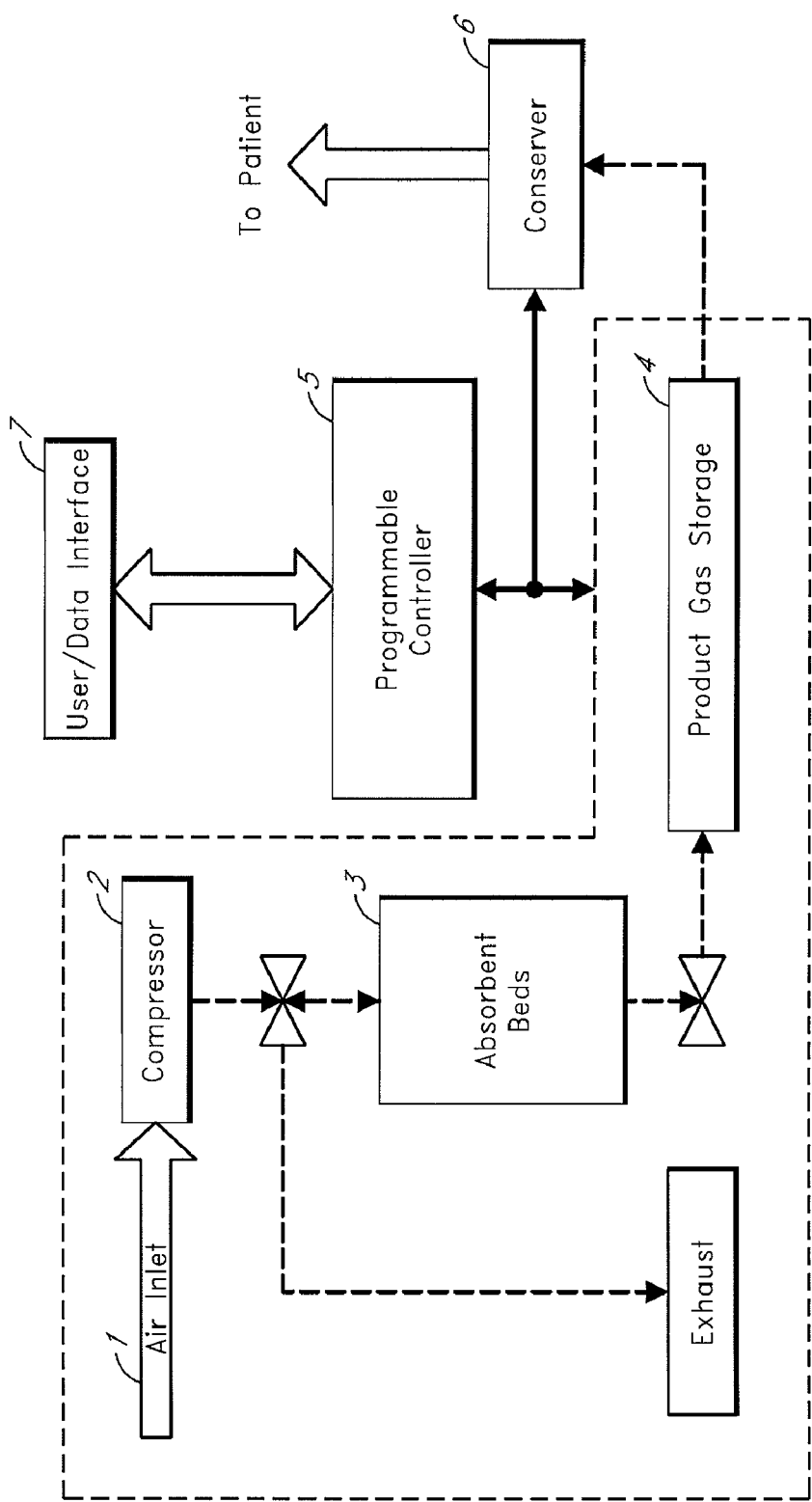
FIG. 1 schematically illustrates an exemplary prior art oxygen concentrator system.
Figure 2:
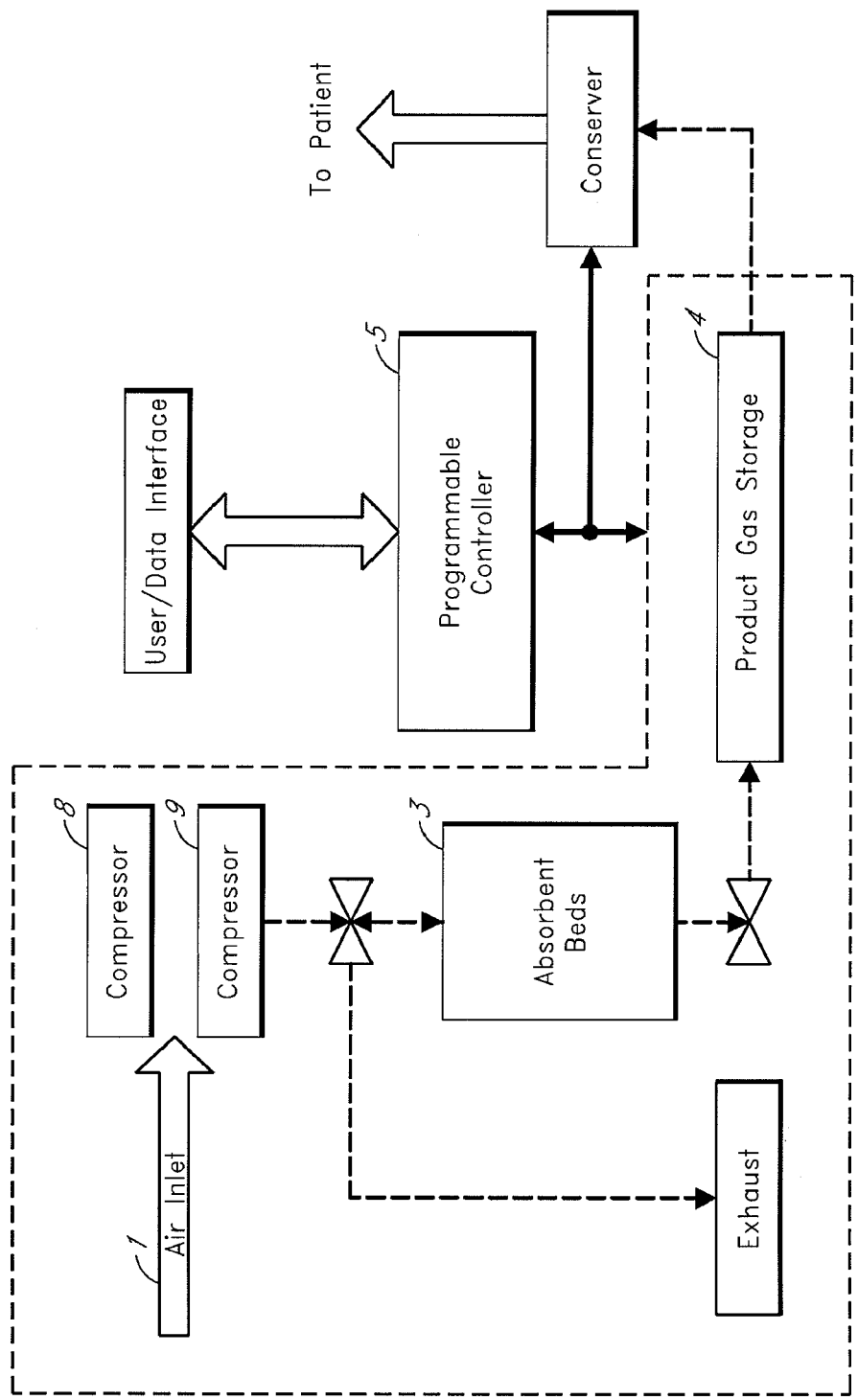
FIG. 2 schematically illustrates an oxygen concentrator system of one preferred embodiments of the present invention.

Referring to FIG. 2, the preferred embodiments of the present invention provide an oxygen concentrator system including provision for at least two compressors 8 and 9, both of which receive input gas from air inlet 1, a PSA section including adsorbent beds 3, gas flow control 6 and exhaust 7, a product gas storage device 4, and a programmable controller 5. In one implementation, the concentrator system may be populated at the time of manufacture with either a single compressor installed, or multiple compressors. The concentrator may be constructed to contain a common frame or a chassis, with provision for population of one or more compressors. In a preferred implementation, the concentrator system is preferably designed so that its product delivery rate is limited, hereinafter referred to as its single compressor product delivery rate, primarily by the feed rate of pressurized air from the compressor. The system is designed such that additional compressors, preferably one additional compressor, may be added to the system to increase the gas feed rate, thereby allowing a greater upper limit to product gas delivery rate. In one version, the second optional compressor occupies a space in the concentrator that may be left empty should the single compressor product delivery rate be sufficient to meet a demand requirement. Without the second compressor, the device is lighter and may be optimally designed for power or battery run time and weight. When the second compressor is added, weight increases and overall system efficiency may decrease, but the capacity of the system will be higher. Not only does the provision for a second compressor allow for a common platform with differing output capacities, it also allows for limiting the number of components that need to be qualified by the Federal Drug Administration, which can be a long and expensive process. Thus higher or lower capacity concentrators may be produced by populating differing numbers of one compressor type, rather than qualifying and maintaining inventory of multiple compressor types of differing capacity.

Figure 3:
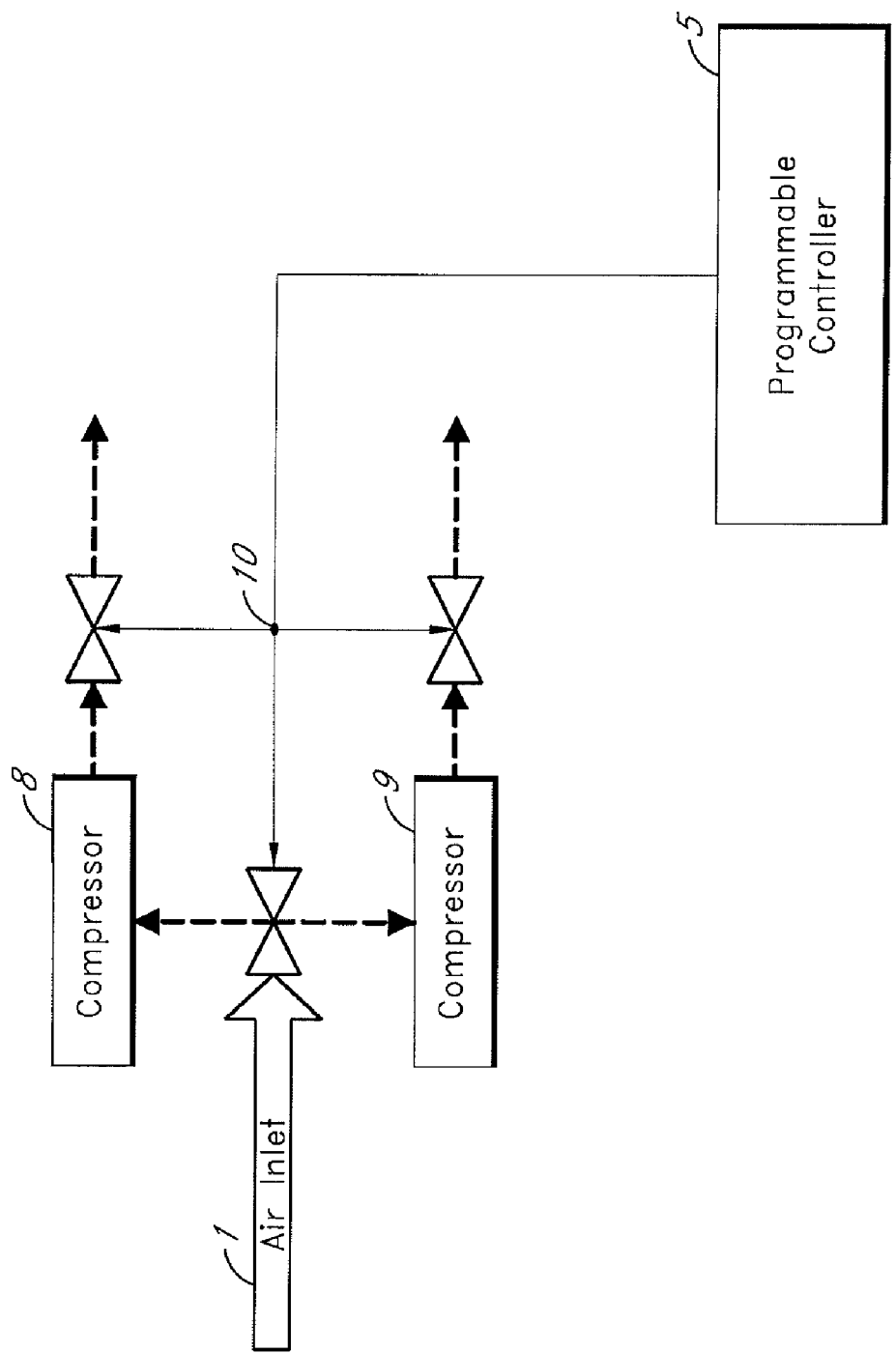
FIG. 3 illustrates varying valve arrangements which may be used to implement an oxygen concentrator system which can operate with one or two compressors populated.
Figure 4:
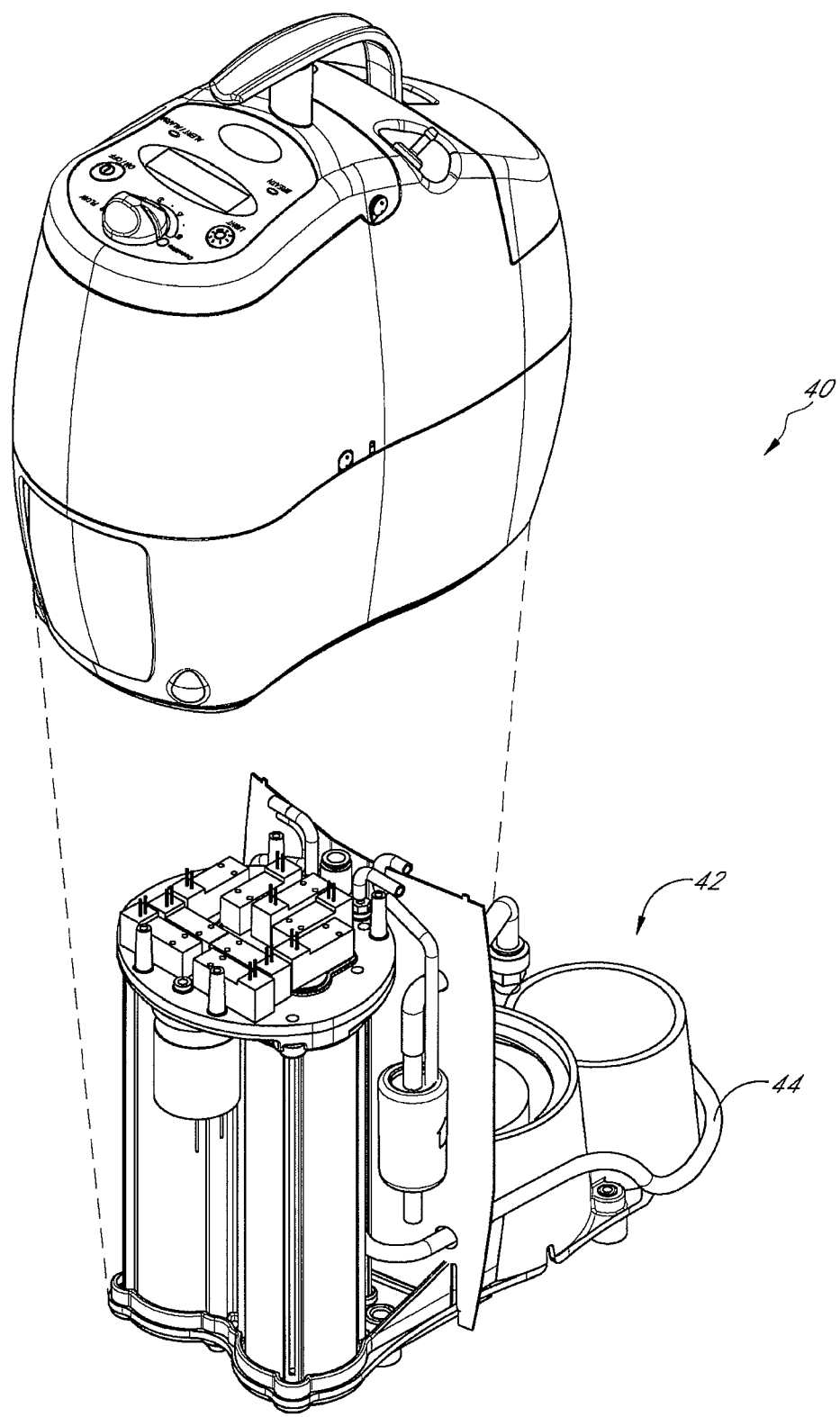
FIG. 4 illustrates an expandable oxygen concentrator device of one preferred embodiment of the present invention.

FIG. 3 illustrates varying valve arrangements 10 may be used to implement an oxygen concentrator system which can operate with one or two compressors populated. Arrangements of more than two compressors are within the scope of the invention, but the case of one or two installed compressor has been found to be useful by the inventors and will be used as an example. Preferably, although not required, controller 5 will control the valve arrangements depending on the number of compressors populated. In one version of the invention, the above concentrator system is configured such that the compressed gas input flow from the second compressor is teed into the flow from the first compressor. In another version, a check valve is present in line between the second compressor and the tee. In another version, both compressors utilize the same drive electronics on the controller. In one implementation, two headers exist on the circuit board with which the two compressor motor leads connect. In another implementation, the system is able to detect the presence of the second compressor, and to change its control algorithms and user interface when it is present. For example, if the single compressor configuration yields 750 ml/min of product gas, the user interface may allow access to five settings. If the dual compressor configuration allows 1350 ml/min of product gas, which is slightly less than twice the single compressor product flow rate due to reduced PSA recovery, the controller may activate controls enabling higher product flow and the user interface may allow access to nine settings.

In another version, the controller may control the two compressors in such a way as to extend life and increase compressor efficiency. Compressor/motor assemblies may be characterized for wear vs. flow and for efficiency vs. flow, and the controller can selectively employ the two compressors such that these parameters are optimized. For example, a rotating motor driving a piston compressor increases flow with operating speed, and typically has greater efficiency at the upper flow ranges of its operating range. For example, when 40% of the maximum feed flow is required, one compressor may be operated by itself at 80% capacity and the other shut off. By using this control method, the specific power across the single compressor product flow range of the system with two compressors may be identical to that of the single compressor. Periodically, the controller may elect to switch compressors such that the total hours accumulated is divided between compressors. As a further feature, the controller, employing sensors within the system, may be able to detect when one compressor's output has declined, and may elect to shut down that compressor until service is possible, while continuing to operate the concentrator (at or below the single compressor maximum product rate) on the remaining compressor.

In another version, the presence of a second compressor may cause the system to operate at a higher peak pressure or a different pressure ratio, increasing the recovery of the PSA cycle.

In another version, the system may have capacity for three or more compressors; addition of each compressor may result in increased product gas output.

In another version, a system 40 may be configured with empty spaces 42 for additional ancillary equipment such as cooling equipment, filters, and tubing connectors which may be required when the supplemental compressor is added. In this way, one product framework, including the majority of components, software, electronics, safety assessment, and regulatory approval, may be constructed. A simple "upgrade kit," including the supplemental compressor(s) and small ancillary parts, may be applied either after market or in a parallel manufacturing line. The multi-compressor version of the product may not perform well on the optimization value curve generated for the single compressor design, but the approach may allow for development of two products in one development cycle. In addition, it may allow for oxygen patients to have a lightweight low flow device when they are more active; as their condition worsens, their equipment may be upgraded to a slightly heavier but higher capacity device.

In another embodiment of this invention, the concentrator may be equipped with an external gas feed port 44. This port may be connected via tubing in a similar fashion to the second compressor from above, teed into the feed line from the first compressor. A check valve or a controllable valve may be placed in line to eliminate flow out of this port. A second external compressor may be operated outside, of the concentrator, a tube may be connected from this compressor to the concentrator and compressed air flow may be directed into concentrator, yielding the ability to produce higher flows of oxygen.

In another version of this embodiment, the concentrator may detect when the external feed of gas is present, and may change its control algorithms accordingly. In one version, it may turn off its internal compressor and rely on the external compressor for feed air. This allows the concentrator to produce gas while deferring use of the internal compressor and electrical systems. In another version, the controller may change the number of flow settings available when external compression is used.

In a further version of this embodiment, the external compressor may be driven by a single-phase AC induction motor, and may or may not be optimally designed for transportability. The compressor may be located within an enclosure, and very simple drive electronics, cooling provisions, and noise abatement may be supplied within the enclosure. Alternatively, the external compressor may be powered by DC electricity, and may be equipped to run off an AC/DC converter, DC power source, or battery.

Although the foregoing description of the preferred embodiments of the present invention has shown, described and pointed out the fundamental novel features of the invention, it will be understood that various omissions, substitutions, and changes in the form of the detail of the invention as illustrated as well as the uses thereof, may be made by those skilled in the art, without departing from the spirit of the invention. Particularly, it will be appreciated that the preferred embodiments of the invention may manifest itself in other shapes and configurations as appropriate for the end use of the article made thereby.

What is claimed is:

1. An oxygen concentrator system, comprising:
    a plurality of compressors;
    a PSA unit in fluid communication with the compressors; and
    a controller, said controller adapted to selectively activate or deactivate one or more of the plurality of compressors to optimize system performance and efficiency,
    wherein each compressor is capable of producing compressed feed gas for the PSA unit, wherein compressed feed gas stream from a first compressor is teed into the compressed feed gas stream from a second compressor.

2. The oxygen concentrator of claim 1, wherein the two compressor feed gas streams are connected by a check valve.

3. The oxygen concentrator system of claim 1, wherein the controller selectively activates more than one compressor to cause multiple compressors to operate at the same time, thereby enabling the system to operate at a higher peak pressure, increase the recovery of the PSA cycle, and expand the product rate.

4. The oxygen concentrator system of claim 1, wherein the controller selectively alternates activation and deactivation of a plurality of compressors to reduce the wear on a single compressor.

5. The oxygen concentrator system of claim 1, wherein at least one of the compressors can be removed from the system when not in use so as to reduce overall weight of the system.

6. The oxygen concentrator system of claim 1, wherein the controller is capable of determining the number of compressors present in the system and adjusting system algorithms and user interface according to the number of compressors present.

7. The oxygen concentrator system of claim 1, wherein the compressors comprise internal and external compressors.

8. The oxygen concentrator system of claim 7, wherein the controller deactivates the internal compressor and utilizes the external compressor for feed gas.

9. The oxygen concentrator system of claim 3, wherein the controller selectively activates more than one compressor simultaneously to increase pressurized gas feed rate, thereby resulting in a higher gas delivery rate.

10. The oxygen concentrator system of claim 1, wherein the controller is capable of detecting and deactivating compressors that require maintenance service.

11. The oxygen concentrator system of claim 1, wherein the plurality of compressors utilize the same drive electronics on the controller.

* * * * *